United States Patent [19]

Koberstein et al.

[11] 4,048,232
[45] Sept. 13, 1977

[54] PROCESS FOR THE PRODUCTION OF 3-METHYLMERCAPTOPROPIONALDE-HYDE

[75] Inventors: Edgar Koberstein, Alzenau; Klaus Müller; Ferdinand Theissen, both of Grossauheim, all of Germany

[73] Assignee: Deutsche Gold- und Silber-Scheideanstalt Vormals Roessler, Frankfurt, Germany

[21] Appl. No.: 399,127

[22] Filed: Sept. 20, 1973

[30] Foreign Application Priority Data

Apr. 21, 1973 Germany ............................ 2320544

[51] Int. Cl.² .............................................. C07C 47/02
[52] U.S. Cl. .............................. 260/601 R; 260/609 B
[58] Field of Search ......................... 260/601 R, 609 B

[56] References Cited

U.S. PATENT DOCUMENTS

| | | | |
|---|---|---|---|
| 2,087,565 | 7/1937 | Bulle et al. | 260/248.5 X |
| 2,485,236 | 10/1949 | Gresham et al. | 260/601 R |
| 2,626,282 | 1/1953 | Cunningham et al. | 260/601 R |
| 2,776,996 | 1/1957 | Hunt | 260/601 R |
| 3,594,425 | 7/1971 | Brader et al. | 260/604 |

FOREIGN PATENT DOCUMENTS

| | | | |
|---|---|---|---|
| 976,673 | 3/1951 | France | 260/601 R |
| 986,198 | 3/1965 | United Kingdom | 260/601 R |

Primary Examiner—Donald G. Daus
Assistant Examiner—D. B. Springer
Attorney, Agent, or Firm—Cushman, Darby & Cushman

[57] ABSTRACT

3-Methylmercaptopropionaldehyde is made from acrolein and methyl mercaptan using hexamethylene tetramine as the catalyst.

8 Claims, No Drawings

PROCESS FOR THE PRODUCTION OF 3-METHYLMERCAPTOPROPIONALDEHYDE

The invention is directed to a process for the production of 3-methylmercaptopropionaldehyde from acrolein and methyl mercaptan in the presence of a catalyst. 3-methylmercaptopropionaldehyde is especially valuable as an intermediate in the preparation of methionine.

It is known to prepare 3-methylmercaptopropionaldehyde by reaction of acrolein with methyl mercaptan. The reaction is carried out in the presence of a catalyst, in a given case at elevated temperature and also in a given case at reduced or elevated pressure. As catalysts there have been used organic bases such as pyridine, quinoline and triethylamine, in a given case in combination with an organic acid such as formic acid, acetic acid or benzoic acid, organic peroxides such as benzoyl peroxide, mercuryl methyl mercaptide or copper (II) acetate (see German Auslegeschrift 1,618,889, particularly column 4, lines 21–36).

In all these cases there is the disadvantage that the 3-methylmercaptopropionaldehyde produced must be freed by a distillation and, in a given case, further purification processes from byproducts and the catalyst in order that it be storage stable or that it be able to be further worked up to methionine without difficulty. The formation of byproducts to be sure can be reduced if the reaction is carried out at lower temperatures, especially temperatures below 30° C., but they are still considerable at these low temperatures. Besides the space-time-yield is less at the lower temperatures.

There has now been found a process for the production of 3-methylmercaptopropionaldehyde from acrolein and methyl mercaptan in the presence of a catalyst wherein the catalyst is hexamethylenetetramine.

The 3-methylmercaptopropionaldehyde is obtained in this process as a colorless, water-white liquid and is as well as free of byproducts. Therefore it can be used further without any purification, especially it can be employed directly for the production of methionine. The process of the invention results in reaction and yields of more than 99%. Since the 3-methylmercaptopropionaldehyde also is produced as well as free of byproducts if the reaction is carried out at high temperatures, namely at temperatures between about 50° and 120° C., these temperatures are selected with advantage and because of the high reaction speeds produce outstanding space-time-yields.

For the reaction according to the invention the methyl mercaptan is added in an at least equivalent amount to the acrolein. It is advantageous to take 1.0 to 1.1 mole of methyl mercaptan, especially 1.01 to 1.05 moles of methyl mercaptan, for each mole of acrolein. For each mole of acrolein there is generally used about 0.001 to 5 weight %, especially 0.01 to 1 weight % of hexamethylenetetramine. There can be used the commercial products, for example a customary water-containing acrolein.

For carrying out the process of the invention advantageously 3-methylmercaptopropionaldehyde is present and there is introduced into this the methyl mercaptan and acrolein either simultaneously or successively. The hexamethylenetetramine can be present either completely or partially with the 3-methylmercaptopropionaldehyde or can be added entirely or partially with the methyl mercaptan.

The reaction can take place suitably at temperatures between about 50° and 120° C., preferably between 75° and 110° C., especially between 80° and 100° C. The pressure can be chosen arbitrarily from a wide range, however it is recommended in order to use simple apparatus to operate at normal pressure or only moderately reduced or elevated pressure. Preferably there are used pressures between 1 and 10 bars.

The 3-methylmercaptopropionaldehyde obtained by the reaction can be further used directly, i.e. without purification. In case the 3-methylmercaptopropionaldehyde is to be stored for long times, it can be advantageous to treat it with water. This can be provided, for example, by a simple wash with 0.01 to 1 part by volume of water for each part by volume of 3-methylmercaptopropionaldehyde.

Unless otherwise indicated all parts and percentages are by weight.

EXAMPLE 1

There was first dissolved in 30 grams of 3-methylmercaptopropionaldehyde 25 mg of hexamethylenetetramine and then with cooling 18.0 grams of methyl mercaptan. This solution and 20.7 grams of acrolein were introduced simultaneously but separately from each other inside 2 minutes in uniform streams into 40 grams of 3-methylmercaptopropionaldehyde preheated to 75° C. The mixture was vigorously stirred during this and for a subsequent 25 minutes. The temperature rose temporarily up to 81° C. The acrolein was essentially completely reacted. The yield of 3-methylmercaptopropionaldehyde based on the acrolein added amounted to 99.2%. The 3-methylmercaptopropionaldehyde had a refractive index $n_D^{20}$ of 1.4815.

EXAMPLE 2

The procedure was the same as in Example 1 except there was used 33.7 grams of acrolein, 29.5 grams of methyl mercaptan and 19.9 mg of hexamethylenetetramine. The reaction temperature was up to 91° C., the reaction time 32 minutes. The acrolein was 99.8% reacted. There was a yield of 99.0% of 3-methylmercaptopropionaldehyde based on the acrolein added. The refractive index was 1.4830.

EXAMPLE 3

The procedure was the same as in Example 1 except there was used 27.6 grams of acrolein, 24.2 grams of methyl mercaptan and 10.0 mg of hexamethylenetetramine. The reaction temperature was up to 79° C., the reaction time 61 minutes. There was a yield of 99.8% of 3-methylmercaptopropionaldehyde based on the acrolein added. The refractive index was 1.4822.

EXAMPLE 4

The procedure was the same as in Example 1 except that there was used 21.8 grams of acrolein, 18.8 grams of methyl mercaptan and 5.2 mg of hexamethylenetetramine. The reaction temperature was up to 78° C., the reaction time 75 minutes. The acrolein was 99.8% reacted. The yield of 3-methylmercaptopropionaldehyde was 99.2% based on the acrolein added. The refractive index was 1.4816.

EXAMPLE 5

There were fed into a continuously operating reactor consisting of an intensive mixing space, a heat exchanger and a circulating pump hourly 2000 ml of 97% acrolein, 1415 grams of 99% methyl mercaptan and 850 ml of a solution of 4.3 grams of hexamethylenetetramine in 97% 3-methylmercaptopropionaldehyde. The reaction took place at 90° C. and 4 bar. There were withdrawn hourly from the cycle 3970 grams of reaction mixture over a pressure regulating apparatus. The reaction amounted to 99% based on the acrolein added. The 3-methylmercaptopropionaldehyde recovered had a purity of 99.8%.

We claim:

1. In a process for the production of 3-methylmercaptopropionaldehyde from acrolein and methyl mercaptan the improvement comprising carrying out the reaction in the presence of hexamethylenetetramine as a catalyst.

2. A process according to claim 1 carried out at a temperature between 50° and 120° C.

3. A process according to claim 2 wherein there is used 0.001 to 5% by weight of hexamethylenetetramine based on the acrolein.

4. A process according to claim 3 wherein there is employed 1.0 to 1.1 mole of methyl mercaptan per mole of acrolein.

5. A process according to claim 4 wherein there is employed 1.01 to 1.05 moles of methyl mercaptan per mole of acrolein and 0.01 to 1% by weight of hexamethylenetetramine based on the acrolein.

6. A process according to claim 5 wherein the pressure is between 1 and 10 bars.

7. A process according to claim 4 wherein the pressure is between 1 and 10 bars.

8. A process according to claim 3 wherein the methyl mercaptan is added in an amount at least equivalent to the acrolein.

* * * * *